United States Patent [19]

Decor

[11] 4,087,465

[45] May 2, 1978

[54] PROCESS FOR THE PREPARATION OF HALOGENO-ACETALS FROM ENOXYSILANES

[75] Inventor: Jean-Pierre Decor, Thurins, France

[73] Assignee: Rhone-Poulenc Industries, Paris, France

[21] Appl. No.: 771,313

[22] Filed: Feb. 23, 1977

[30] Foreign Application Priority Data

Feb. 25, 1976 France .................................. 76 05242
Jan. 13, 1977 France .................................. 77 00855

[51] Int. Cl.$^2$ ............................................. C07C 41/00
[52] U.S. Cl. ................................ 260/615 A; 260/338; 260/340.7; 260/340.9 R; 260/598
[58] Field of Search ................ 260/615 A, 338, 340.7, 260/340.9

[56] References Cited

U.S. PATENT DOCUMENTS 2,695,318  11/1954  Thiele .............................. 260/615 A

FOREIGN PATENT DOCUMENTS 691,820  5/1953  United Kingdom ............ 260/615 A

*Primary Examiner*—Howard T. Mars
*Attorney, Agent, or Firm*—Stevens, Davis, Miller & Mosher

[57] ABSTRACT

Halogeno-acetals of ethylenic aldehydes are made by reaction of a corresponding enoxysilane compound with a halogen cation and an alcohol. The products are useful inter alia in the synthesis of retinal and other unsaturated aldehydes.

11 Claims, No Drawings

PROCESS FOR THE PREPARATION OF HALOGENO-ACETALS FROM ENOXYSILANES

The present invention provides a process for the preparation of halogeno-acetals of ethylenically unsaturated aldehydes of the general formula:

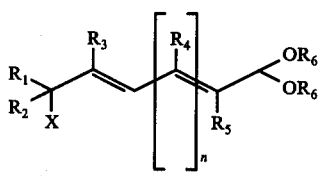
(I)

in which X represents chlorine, bromine or iodine, $R_1$, $R_2$, $R_3$, $R_4$ and $R_5$, which may be identical or different, represent hydrogen, straight or branched alkyl of 1 to 6 carbon atoms, especially methyl or ethyl, or straight or branched alkenyl of 3 to 6 carbon atoms, in which the double bond is in a position other than the 1-2 position, $n$ is 0, 1, 2, 3 or 4, it being understood that if $n$ is greater than 1, the various symbols $R_4$ may be identical or different, and the symbols $R_6$ each represent straight or branched alkyl of 1 to 6 carbon atoms, especially methyl or ethyl, or they together form a straight or branched alkylene radical $R'_6$ of 2 to 6 carbon atoms, optionally substituted by hydroxyl or alkoxy of 1 to 4 carbon atoms, especially a —$CH_2$—$CH_2$— radical. The term halogen as used below, includes only chlorine, bromine and iodine.

The halogeno-acetals of formula I are particularly useful as intermediates in organic synthesis. Thus they can be used to introduce an $\alpha,\beta$- ethylenically unsaturated aldehyde unit into a monoene or polyene radical by reaction with a polyene sulphone in the presence of an alkaline agent in accordance with the process described in Belgian Pat. No. 794,872, the sulphone resulting from this condensation being subsequently desulphonated with the formation of a further double bond.

In particular, retinal (the aldehyde of vitamin A) can be prepared by the action of 1-bromo-2-methyl-4,4-diethoxy-2-butene on phenyl 5-(2,6,6-trimethyl-1-cyclohexenyl)-3-methyl-2,4-pentadienyl sulphone, followed by desulphonation of the phenyl-sulphonyl 9-(2,6,6-trimethyl-1-cyclohexenyl)-1,1-diethoxy-3,7-dimethyl-2,6,8-nonatriene thus obtained, to give retinal.

It is known that $\gamma$-halogeno-acetals of ethylenically $\alpha,\beta$-unsaturated aldehydes can be prepared by halogeno-alkylation of a 1-alkoxy-1,3-diene by the action of an N-halogeno-succinimide in the presence of an alcohol, in accordance with the process described by S. M. MAKIN et al., J. Gen. Chem. USSR, 32, 1088 (1962). However this process has the disadvantage that the ethylenically di-unsaturated ethers used as starting materials are accessible only with difficulty; indeed, they are generally prepared by treating acetals of ethylenically $\alpha,\beta$-unsaturated or $\beta,\gamma$-unsaturated aldehydes at high temperature in the presence of catalysts, the raw materials used being themselves difficult to synthesise. Although the method of MAKIN can also be applied to the synthesis of $\omega$-halogeno-acetals of aldehydes containing a system of conjugated double bonds, the preparation of such products by this method presents very great problems because of the difficulty of access to the necessary raw materials.

The process according to the invention allows these difficulties to be overcome and makes it possible to obtain unsaturated halogeno-acetals of aldehydes in good yield, starting from easily accessible raw materials.

According to the present invention, the halogeno-acetals of ethylenically unsaturated aldehydes of the formula (I) are prepared by reacting a halogen cation chosen from $Cl^+$, $Br^+$ and $I^+$, with an enoxysilane of the formula:

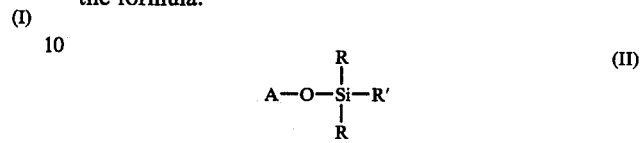
(II)

in which A represents a radical of the general formula:

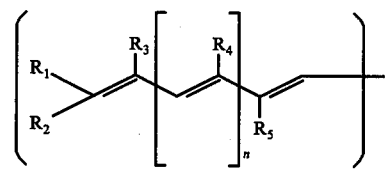

in which $R_1$, $R_2$, $R_3$, $R_4$, $R_5$ and $n$ are as defined above, R represents straight or branched alkyl of 1 to 12 carbon atoms, especially methyl or ethyl, cycloalkyl of 3 to 6 carbon atoms, phenyl, alkylphenyl of which the alkyl contains 1 to 6 carbon atoms, or phenylalkyl of which the alkyl contains 1 to 6 carbon atoms, and R' is identical to R or represents a radical of the formula:

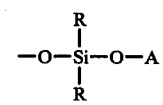

in which R and A are as defined above, and reacting the product with a primary or secondary alcohol of the formula $R_6OH$ in which $R_6$ is as defined above, or with a glycol of the general formula HO—$R'_6$—OH in which $R'_6$ is as defined above.

Halogen cations have been known for many years and have been described in, for example, the article by J. AROTSKY and M. C. R. SYMONS, Quart. Rev., 16, 282 (1962).

Halogen cations can be detected by various methods, such as, for example, conductivity measurement and mass spectrometry. Many products are known to be sources of halogen cations [Peter B. D. de La Marre, "Electrophylic Halogenation", Cambridge Chemistry Texts, 1976]. Compounds in which a halogen atom is attached by a covalent bond to another halogen atom or to a nitrogen or oxygen atom constitute a class of products which may be used as sources of halogen cations; by way of example there may be mentioned alkali metal hypohalites, organic hypohalites, N-halogeno-amines, N-halogeno-amides, N-halogeno-carbo-imides, N-halogeno-sulpho-imides, N-halogeno-carbo-sulpho-imides, N-halogeno-hydantoins and N-halogeno-triazoles and benzotriazoles. The compounds resulting from addition of molecular halogen to aliphatic, aromatic or cyclic quaternary ammonium halides, or to aromatic halides, constitute a second class of products which may be used as sources of halogen cations. The complexes formed by the action of molecular halogen on an aliphatic or cyclic amide constitute a third class of compounds which may be used as sources of halogen cations.

As sources of halogen cations there may be especially mentioned alkali metal hypohalites, organic hypohalites, in particular hypohalites of saturated tertiary aliphatic alcohols containing up to 13 carbon atoms, N-chloro and N-bromo-succinimides, N-bromo and N-chloro-polymaleimides, N-bromo and N-chloro-caprolactams, 1,3-dichloro- and 1,3-dibromo-5,5-dimethyl-hydantoins, N-bromo and N-chloro saccharins, chlorobenzotriazole, N-bromo-acetamide, bromourea, chloramine, phenyl-trimethylammonium perbromide, tetrachloro-tetra-n-butylammonium iodide, dichloro-tetra-n-butylammonium iodide, tetra-n-butylammonium tribromide, pyridinium perbromide, iodobenzene dichloride and complexes formed by the action of chlorine, bromine or iodine on dimethylformamide, dimethylacetamide and N-methyl-pyrrolidone.

In general terms it is sufficient to react one halogen cation per mol of enoxysilane of the formula (II), that is to say to use the quantity of compound necessary to provide one halogen cation per mol of enoxysilane of the formula (II), although an excess of one or other of these reagents can be used without any disadvantages. Also in general terms, the reaction between the halogen cation and the enoxysilane of the formula (II) may take place in the presence of an excess of the alcohol of the formula $R_6OH$, or of the glycol of the formula $HO—R'_6—OH$. Such conditions allow the halogenation and dialkoxylation of the enoxysilane of the formula (II) to be carried out in a single stage. The temperature of the reaction is not critical and can, for example, be between −40° and +80° C, and preferably between −20° and +20° C, in order to avoid appreciable decomposition of the products.

If compounds in which a halogen atom is attached by a covalent bond to another halogen atom or to a nitrogen or oxygen atom, or a compound resulting from the addition of a molecular halogen to an aliphatic, aromatic or cyclic quaternary ammonium halide or to an aromatic halide, are used as the source of the halogen cation, the reaction is generally carried out at a temperature of between −40° and +80° C, depending on the stability of the product used as the source of halogen cation, and in particular between −20° and +30° C. Usually, the product which generates the halogen cation is added to a solution of the enoxysilane of the formula (II) in an excess of alcohol of the formula $R_6OH$ or an excess of glycol of the formula $HO—R'_6—OH$. In order to speed up the reaction rate, it is advantageous to carry out the reaction in the presence of a catalytic quantity of a strong organic or inorganic acid known to be a catalyst for acetal formation, such as hydrochloric, sulphuric and methanesulphonic acid; this acid may be introduced into the reaction mixture at the start of the reaction or only after the reaction of the compound which generates the halogen cation with the enoxysilane of the formula (II).

More particularly, if a hypohalite of a saturated tertiary aliphatic alcohol is used as the source of halogen cations, it is preferable to use a hypohalite derived from tert.-butanol, for reasons of availability. Generally, the hypohalite of a saturated tertiary aliphatic alcohol is used in the form of a solution in an organic solvent which is inert under the reaction conditions, such as a lower liquid aliphatic hydrocarbon, for example pentane, an aromatic hydrocarbon, for example benzene, toluene or a xylene, or a halogenated aliphatic or aromatic hydrocarbon.

If a complex formed by the action of a molecular halogen on an aliphatic or cyclic amide is used as the source of halogen cations, the said complex is generally prepared in situ by the addition of the halogen to an excess of the amide in a solution of the enoxysilane of the formula (II) in the alcohol of the formula $R_6OH$ or in the glycol of the formula $HO—R'_6—OH$. Usually, the reaction is carried out at a temperature of between −40° and +40° C and preferably between about −20° and +20° C. However, it is often advantageous to prepare the halogen/amide complex in an excess of amide used as the solvent for the enoxysilane of the formula (II) and subsequently to react an excess of the alcohol of the formula $R_6OH$, or of the glycol of the formula $HO—R'_6—OH$, with the halogeno-immonium halide resulting from the action of the halogen/amide complex on the enoxysilane of the formula (II). No matter which operating procedure is followed, it is sufficient to employ 1 mol of halogen per mol of enoxysilane of the general formula (II).

The enoxysilanes of the general formula (II), in which R' is identical to R, used as raw materials, can be prepared by applying the method described in Belgian Pat. No. 670,769 which consists of reacting the enolisable aldehyde corresponding to the radical A with a halogenosilane of the general formula Hal—Si (R)$_3$ in which Hal represents a halogen atom and R is defined as above. The enoxysilanes of the general formula (II), in which R' represents a radical

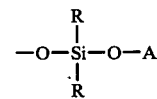

can be prepared in accordance with the same method by reaction of the aldehyde corresponding to the radical A with a dihalogeno-silane of the general formula:

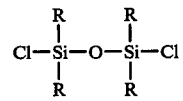

The process of the present invention is particularly suitable for the preparation of 1,1-dimethoxy-3-methyl-4-chloro-2-butene and 1,1-dimethoxy-3-methyl-4-bromo-2-butene from 1-trimethylsilyloxy-3-methyl-1,3-butadiene; the yields reach 85% and the product obtained is mostly made up of the trans isomer, which represents a very particular advantage when this product is used in the preparation of retinal (the aldehyde of vitamin A) in accordance with the process described in Belgian Pat. No. 794,872.

The following Examples illustrate the invention.

EXAMPLE 1

26.5 cm$^3$ of a 2.25 molar solution of tert.-butyl hypochlorite in pentane are added, over a period of 90 minutes, to a solution of 9.36 g. (6 × 10$^{-2}$ mols) of 1-trimethylsilyloxy-3-methyl-1,3-butadiene in 50 cm$^3$ of methanol, cooled to −20° C. On completion of the addition, one drop of concentrated hydrochloric acid is added and then the temperature is allowed to rise to about 20° C. 80 cm$^3$ of water are then added to the mixture which is transferred to a separating funnel. The reaction flask is rinsed with 25 cm³ of pentane which is added to the contents of the separating funnel. The aqueous phase is separated and then extracted 3 times with a total of 75 cm³ of pentane, which is combined with the decanted organic phase. The organic extracts are washed twice with a total of 50 cm³ of water. After drying over sodium sulphate and filtering, the solution is made up to 250 cm³ by the addition of pentane. An aliquot portion of 25 cm³ is concentrated to dryness under reduced pressure (20 mm. of mercury) at about 20° C. In this way, a residue weighing 1.1403 g. is obtained which contains, as measured by nuclear magnetic resonance, 73.7% by weight of cis and trans 1,1-dimethoxy-3-methyl-4-chloro-2-butene, which corresponds to a yield of 85.1%, based on the starting 1-trimethylsilyloxy-3-methyl-1,3-butadiene.

The solution of tert.-butyl hypochlorite in pentane can be prepared in the following way. A mixture of 10.95 g. (0.148 mol) of tert.-butanol and 9.80 g. (0.163 mol) of acetic acid are added at 2° C., and over a period of 5 minutes to 190 cm³ of an aqueous sodium hypochlorite solution containing 0.148 mol of NaOCl. After the completion of the addition, the reaction mixture is maintained at 2° C., with stirring for 10 minutes. After the addition of 20 cm³ of pentane, the organic phase is decanted, washed with 20 cm³ of an aqueous sodium bicarbonate solution and then with 20 cm³ of water, dried over calcium chloride, and then made up to 50 cm³ by the addition of pentane. In this way, 50 cm³ of a 2.25 molar tert.-butyl hypochlorite solution in pentane are obtained.

EXAMPLE 2

25.8 cm³ of a 2.32 molar solution of tert.-butyl hypochlorite in pentane are added, over a period of 90 minutes, to a solution of 8.52 g. (6 × 10⁻² mols) of 1-trimethylsilyloxy-1,3-butadiene in 50 cm³ of methanol, cooled to −20° C. On completion of the addition, one drop of concentrated hydrochloric acid is added and then the temperature is allowed to rise to 20° C., over a period of 40 minutes. 20 cm³ of a saturated aqueous sodium bicarbonate solution and 80 cm³ of water are then added. The aqueous phase is decanted and then extracted 3 times with a total of 75 cm³ of pentane, which is combined with the organic phase. The organic extracts are washed with 25 cm³ of water and then with 25 cm³ of saturated aqueous sodium bicarbonate solution. After concentrating to dryness under reduced pressure (20 mm. of mercury) at about 20° C., a residue weighing 10.09 g. is obtained, which contains, as measured by nuclear magnetic resonance, 70.7% of trans-4-chloro-1,1-dimethoxy-2-butene, 25.4% of hexamethyldisiloxane and 4% of pentane. The yield of measured 4-chloro-1,1-dimethoxy-2-butene is 79%. The pure product, b.p. 25° C./0.3 mm.Hg., is obtained by distillation under reduced pressure.

The starting 1-trimethylsilyloxy-1,3-butadiene can be prepared by the process described in Belgian Pat. No. 670,769. The product obtained is a mixture consisting of 20% of the cis isomer and 80% of the trans isomer.

EXAMPLE 3

24 cm³ of a 2.5 molar solution of tert.-butyl hypochlorite in pentane are added over a period of 90 minutes to a solution of 8.1 g. (3 × 10⁻² mols) of tetramethyl-di-(1,3-butadiene-1-yl)-disiloxane in 50 cm³ of methanol, cooled to −20° C. On completion of the addition, 1 drop of concentrated hydrochloric acid is added and the temperature is then allowed to rise to about 20° C. 6.42 g. of trans 1,1-dimethoxy-3-methyl-4-chloro-2-butene, b.p. 28°–30° C./0.5 mm.Hg., are obtained after the treatments described in Example 1 and after distillation under reduced pressure.

The starting tetramethyl-di-(1,3-butadien-1-yl)disiloxane (b.p. 87° C./2.5 mm.Hg.) can be prepared, by the method described in Belgian Pat. No. 670,769, by the action of tetramethyl-dichloro-disiloxane on crotonaldehyde.

EXAMPLE 4

19.7 cm³ of a 2.54 molar solution of tert.-butyl hypochlorite in pentane are added over a period of 90 minutes to a solution of 11.2 g. (5 × 10⁻² mols) of a mixture of 3,7-dimethyl-1-trimethylsilyloxy-1,3,6-octatriene and 7-methyl-3-methylene-1-trimethylsilyloxy-1,6-octadiene in 50 cm³ of methanol cooled to −20° C. On completion of the addition, one drop of concentrated hydrochloric acid is added, the temperature is then allowed to rise to about 20° C. 9.15 g. of a colourless liquid, b.p. 85°–87.5° C./0.4–0.5 mm.Hg., are obtained after the treatments described in Example 1 and after distillation under reduced pressure, which liquid is identified by nuclear magnetic resonance and mass spectrography as a mixture of 4-chloro-3,7-dimethyl-1,1-dimethoxy-2,6-octadiene and 3-chloromethyl-7-methyl-1,1-dimethoxy-2,6-octadiene which can be separated by distillation under reduced pressure.

EXAMPLE 5

4.05 g. of 1-trimethylsilyloxy-3-methyl-1,3-butadiene of 95% purity (2.46 × 10⁻² mols) and 25 cm³ of dimethylformamide are introduced into a flask previously purged with a stream of dry nitrogen. 4.0 g. of bromine (2.5 × 10⁻² mols) are added to the mixture, cooled to −20° C., with stirring and over a period of 35 minutes, and stirring is then continued for 10 minutes. 25 cm³ of methanol are added over a period of 15 minutes, while the temperature is maintained at −20° C., and stirring of the reaction mixture is continued for a further 90 minutes while the temperature is allowed to rise to about 20° C. The reaction mixture is then poured into an iced solution of 6.9 g. of sodium bicarbonate in 100 cm³ of water, which causes the evolution of carbon dioxide. When this has ceased, the mixture is extracted 3 times with a total of 150 cm³ of pentane and the organic extracts are dried over sodium bicarbonate and then concentrated under reduced pressure. In this way a colourless liquid residue weighing 4.73 g. is obtained which contains, as measured by nuclear magnetic resonance, 23.5% of cis 1,1-dimethoxy-3-methyl-4-bromo-2-butene and 58.9% of trans 1,1-dimethoxy-3-methyl-4-bromo-2-butene. The overall yield of 1,1-dimethoxy-3-methyl-4-bromo-2-butene is 75.8% based on the starting 1-trimethylsilyloxy-3-methyl-1,3-butadiene.

I claim:

1. Process for the preparation of a halogeno-acetal of an ethylenically unsaturated aldehyde of the formula:

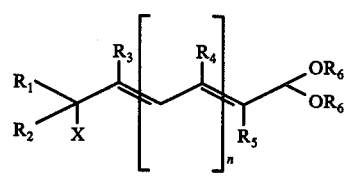

in which: X represents chlorine, bromine or iodine, $R_1$, $R_2$, $R_3$, $R_4$ and $R_5$, which may be identical or different, represent hydrogen, straight or branched alkyl of 1 to 6 carbon atoms, or straight or branched alkenyl of 3 to 6 carbon atoms in which the double bond is in a position other than the 1-2 position, $n$ is 0, 1, 2, 3 or 4, it being understood that if $n$ is greater than 1, the various symbols $R_4$ may be identical or different, and the two symbols $R_6$ each represent straight or branched alkyl of 1 to 6 carbon atoms, or they together form a straight or branched alkylene radical $R'_6$ of 2 to 6 carbon atoms, optionally substituted by hydroxyl or alkoxy of 1 to 4 carbon atoms, which comprises reacting a halogen cation chosen from $Cl^+$, $Br^+$ and $I^+$ with an enoxysilane of the formula:

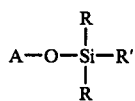

in which A represents a radical of the formula:

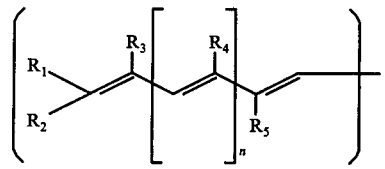

in which $R_1$, $R_2$, $R_3$, $R_4$, $R_5$ and $n$ are defined as above, R represents straight or branched alkyl of 1 to 12 carbon atoms, cycloalkyl of 3 to 6 carbon atoms, phenyl, alkylphenyl of which the alkyl contains 1 to 6 carbon atoms, or phenylalkyl of which the alkyl contains 1 to 6 carbon atoms, and R' is identical to R or represents a radical of the general formula:

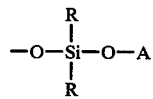

in which R and A are as defined above, in the proportion of one halogen cation per mol of the enoxysilane at a temperature of $-40°$ to $+80°$ C and in the presence of an excess of a primary or secondary alcohol of the formula $R_6OH$ in which $R_6$ is as defined above, or of a glycol of the formula $HO-R'_6-OH$ in which $R'_6$ is as defined above.

2. Process according to claim 1, in which the source of the halogen cation is an alkali metal hypohalite, an organic hypohalite, an N-halogenoamine, an N-halogenoamide, an N-halogeno-carbo-imide, an N-halogeno-sulpho-imide, an N-halogeno-carbo-sulpho-Imide, an N-halogeno-hydantoin, an N-halogeno-triazole or -benzotriazole, pyridinium perbromide, tetrachloro-tetra-n-butylammonium iodide, dichloro-tetra-n-butylammonium iodide, tetra-n-butylammonium tribromide, iodobenzene dichloride, or a complex formed by the action of a molecular halogen on dimethylformamide, dimethylacetamide or N-methylpyrrolidone.

3. Process according to claim 1 in which the source of the halogen cation is a compound in which a halogen atom is attached by a covalent bond to an atom of a different halogen or to a nitrogen or oxygen atom.

4. Process according to claim 1, in which the source of the halogen cation is a hypohalite of a saturated tertiary aliphatic alcohol of 4 to 13 carbon atoms.

5. Process according to claim 1, in which the source of the halogen cation is an N-halogeno-succinimide.

6. Process according to claim 1 in which the source of the halogen cation is a product resulting from the addition of a molecular halogen to an aliphatic, aromatic or cyclic quaternary ammonium halide or to an aromatic halide.

7. Process according to claim 1 in which the source of the halogen cation is a complex formed by the action of a molecular halogen on an aliphatic or cyclic amide in which the nitrogen atom is tertiary.

8. Process according to claim 1, in which the source of the halogen cation is tert-butyl hypochlorite or the complex formed by the action of bromine on dimethylformamide.

9. Process according to claim 1 in which $R_6$ is straight or branched alkyl of 1 to 6 carbon atoms, the source of the halogen cation is an N-halogeno-succinimide or a hypohalite of a saturated tertiary aliphatic alcohol, and the reaction is carried out in the presence of a primary alcohol of formula $R_6OH$.

10. Process according to claim 1 in which X represents chlorine or bromine, $R_1$, $R_2$, and $R_5$ are hydrogen, $R_3$ is methyl, $n$ is 0, and $R_6$ is methyl or ethyl.

11. Process according to claim 1 in which the reaction is carried out in the presence of a catalytic amount of a strong inorganic acid.

* * * * *